United States Patent [19]
Kellogg et al.

[11] Patent Number: 5,897,569
[45] Date of Patent: Apr. 27, 1999

[54] ULTRASONIC GENERATOR WITH SUPERVISORY CONTROL CIRCUITRY

[75] Inventors: Scott Kellogg, Esmond, R.I.; Stephen J. Alam, North Attleboro, Mass.

[73] Assignee: Ethicon Endo-Surgery, Inc., Cincinnati, Ohio

[21] Appl. No.: 08/842,743

[22] Filed: Apr. 16, 1997

[51] Int. Cl.⁶ ................................................ A61B 17/32
[52] U.S. Cl. .......................... 606/169; 604/22; 310/316
[58] Field of Search ................................... 606/169, 171; 310/313–317; 604/22

[56] References Cited

U.S. PATENT DOCUMENTS

| | | | |
|---|---|---|---|
| 4,175,242 | 11/1979 | Kleinschmidt . | |
| 4,979,952 | 12/1990 | Kubota et al. | 606/169 |
| 5,026,387 | 6/1991 | Thomas | 604/22 |
| 5,151,085 | 9/1992 | Sakurai et al. | 604/22 |

Primary Examiner—Michael Buiz
Assistant Examiner—William W Lewis

[57] ABSTRACT

A generator of ultrasonic signals for a transducer which incorporates at least a phase lock loop feedback system for purposes of maintaining the output frequency between first and second voltage values also incorporates supervisory control circuitry for monitoring whether or not the generator and the transducer continue to operate in a resonant condition. In the event that the generator and transducer fail to stay in a resonant condition, the supervisory circuitry will super-impose a control voltage on the phase lock loop feedback path for the purpose of restoring the generator and the transducer to a resonant condition. To reduce the time to return to resonance, a representation of the last resonant frequency can be stored by the supervisory circuitry. When a loss of resonance is detected, the prestored value can be retrieved and superimposed on the phase lock loop feedback circuit for purposes of more quickly restoring the generator and the transducer to resonance.

33 Claims, 7 Drawing Sheets

5,897,569

ULTRASONIC GENERATOR WITH SUPERVISORY CONTROL CIRCUITRY

FIELD OF THE INVENTION

The invention pertains to a system and method for generating ultrasonic signals for use in energizing a transducer assembly at a resonant frequency. More particularly, the invention pertains to an ultrasonic generator which incorporates a phase lock frequency control loop and which further incorporates supervisory circuitry to automatically detect a non-resonant condition and to re-establish resonance.

BACKGROUND OF THE INVENTION

Ultrasonic surgical systems which can be used for the purpose of carrying out surgical functions, such as cutting or coagulating, are known. Such systems usually incorporate a generator that produces electrical signals which excite a transducer assembly mounted in a handpiece assembly.

The transducer assembly is usually coupled to a transmission component, such as an end effector, for carrying out a desired function. The transmission component coupled to the transducer assembly can be of varying lengths.

As the transmission component is subjected to varying environmental conditions, temperature characteristics may vary with the result that a given generator may function at suboptimal operating conditions. Further, as the length of the transmission component coupled to the transducer is increased, additional undesirable oscillatory nodes may occur along the transmission component.

There continues to be a need for generators which will function when transmission components are exposed to substantially temperature invariant characteristics over time and will also control undesirable oscillatory motion.

SUMMARY OF THE INVENTION

The devices and method in accordance with the present invention increase the performance of ultrasonic surgical systems. The device and methods are capable of driving longer ultrasonic transmission components and can drive transmission components that have different fundamental frequencies.

One device in accordance with the present invention includes a generator that incorporates a voltage controlled oscillator in combination with a feedback loop which controls the output frequency of the oscillator in a normal operational mode along with a supervisory control circuit. The supervisory control circuit is adapted to detect, in one embodiment, an undesired operational mode and, in response thereto, to apply a supervisory and overriding control signal to the oscillator for the purpose of restoring a predetermined phase condition. When the normal operational mode has been restored, the supervisory control circuit disconnects or isolates itself from the remaining circuitry thereby enabling the feedback loop to regain control of the output of the oscillator.

For example, when the generator is intended to drive an ultrasonic transducer at a resonant frequency, a normal operational mode would correspond to operating in a resonant condition. An undesired condition, in this instance would be indicated by a loss of resonance.

In one aspect of the present invention, the supervisory control circuitry includes a sensor circuit for detecting an electrical parameter of the feedback signal, such as, for example, phase. The sensor circuit is in turn coupled to control circuitry. The control circuitry incorporates an enable output and a magnitude output.

In response to sensing a loss of a predetermined phase condition in the oscillator, an enable signal is provided by the control unit. This signal in turn couples the magnitude output to a voltage controlled oscillator. The magnitude output provided by the supervisory control circuitry in turn supersedes feedback signals from the feedback loop with a supervisory control value or values.

The superimposed control value can be used to re-establish resonance. In one embodiment, the supervisory control circuitry can set the magnitude of the output control value to one which corresponds to a feedback signal for the most recent resonant frequency condition. The magnitude of the control value can then be varied to re-establish resonance.

Once resonance has been re-established, the control circuitry automatically isolates itself from the feedback control loop which then maintains the output frequency of the oscillator at the resonant value.

The present invention makes it possible to provide electrical signals to and to drive transducers and associated mechanical systems without locking onto undesirable, non-fundamental modes of vibration. Further, acquisition time to establish resonance can be reduced by starting from output control magnitudes corresponding to a known resonant frequency thereby reducing the range of frequencies which must be transversed before a resonant condition is again established.

In another aspect, the control circuitry can incorporate a digital-to-analog converter which provides analog control signals. The digital-to-analog converter can be used as a form of a programmable frequency generator for the purpose of identifying acoustic systems with unique resonance profiles. Additionally, this circuitry can be used as a sweep generator for evaluating acoustic system performance. Finally, the control circuitry, including the digital-to-analog converter circuitry can be used to provide a form of electronic brake to the associated acoustic system by interrupting resonance when it is necessary to immediately reduce or stop transducer motion.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

Figure 1:
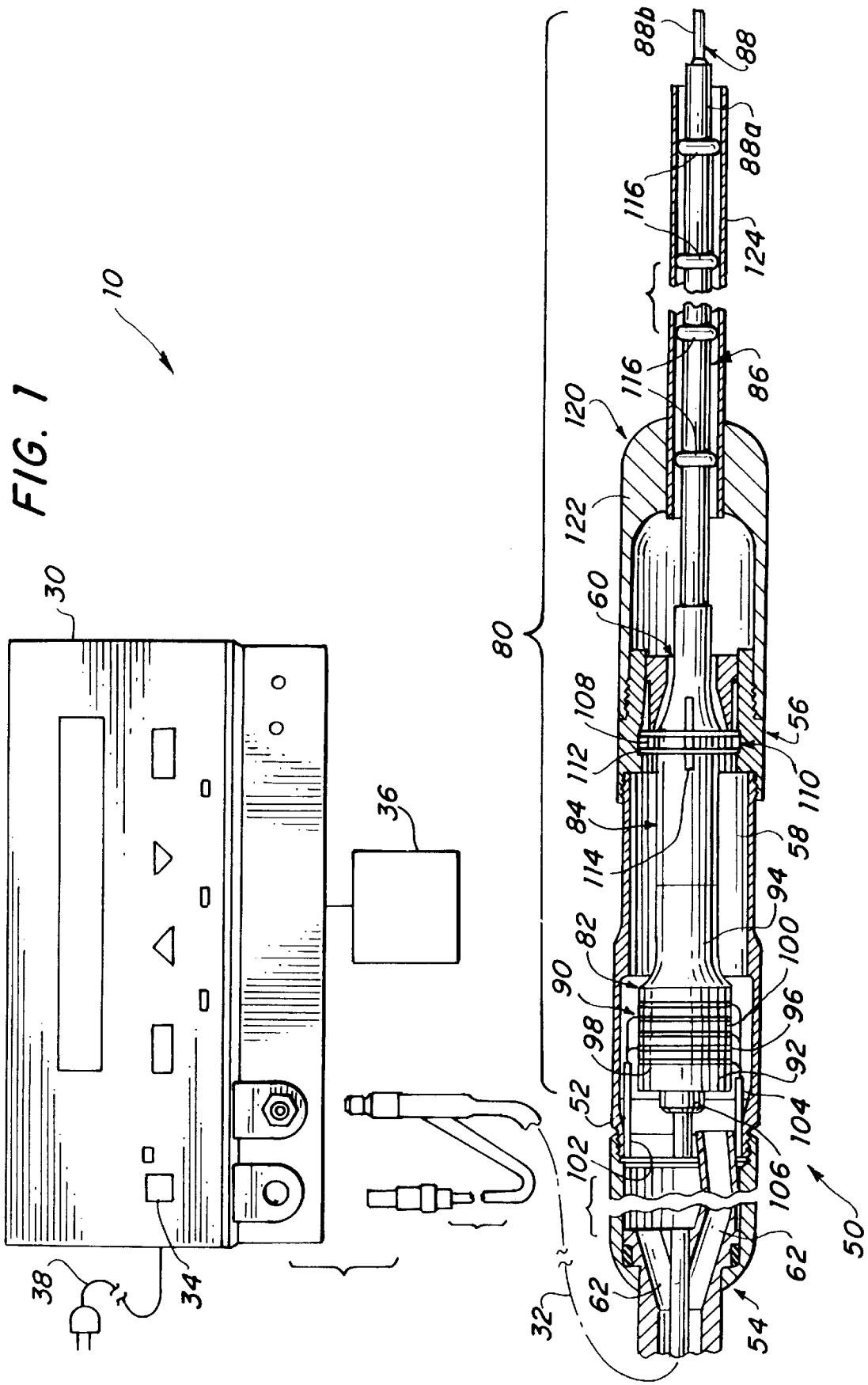
FIG. 1 is a fragmentary view and in partial cross-section of an embodiment of an ultrasonic system.

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

FIG. 1 illustrates a surgical system 10. The surgical system 10 generally includes a generator 30, a handpiece assembly 50, and an acoustic or transmission assembly 80. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude.

An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 1, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase lock loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude at the end effector 88 of the acoustic assembly 80.

The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transducer assembly 82 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery.

Referring still to FIG. 1, the handpiece assembly 50 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. high impact polystyrene or polypropylene). A suitable handpiece assembly 50 is Model No. HP050, available from Ethicon Endo-Surgery, Inc.

The handpiece assembly 50 generally includes a proximal end 54, a distal end 56, and centrally disposed axial opening or cavity 58 extending longitudinally therein. The distal end 56 of the handpiece assembly 50 includes an opening 60 configured to allow the acoustic assembly 80 of the surgical system 10 to extend therethrough, and the proximal end 54 of the handpiece assembly 50 is coupled to the generator 30 by a cable 32. The cable 32 may include ducts or vents 62 to allow air to be introduced into the handpiece assembly 50 to cool the transducer assembly 82 of the acoustic assembly 80.

Referring still to FIG. 1, the acoustic assembly 80 generally includes a transducer stack or assembly 82 and a transmission component or working member. The transmission component may include a mounting device 84, a transmission rod or waveguide 86, and an end effector or applicator 88. The transducer assembly 82, mounting device 84, transmission rod 86, and the end effector 88 are preferably acoustically tuned such that the length of each component is an integral number of one-half system wavelengths ($n\lambda/2$) where the system wavelength $\lambda$ is the wavelength of a preselected or operating longitudinal vibration frequency f of the acoustic assembly 80. It is also contemplated that the acoustic assembly 80 may incorporate any suitable arrangement of acoustic elements. For example, the acoustic assembly 80 may comprise a transducer assembly and an end effector (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda/4$).

As shown in FIG. 1, the transducer assembly 82 of the acoustic assembly 80, which is known as a "Langevin stack", generally includes a transduction portion 90, a first resonator 92, and a second resonator 94. The transducer assembly 82 is preferably an integral number of one-half system wavelengths ($n\lambda/2$) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulas of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section of alternating positive electrodes 96 and negative electrodes 98, with piezoelectric elements 100 alternating between the electrodes 96 and 98. The piezoelectric elements 100 may be fabricated from any suitable material, such as, for example, lead zirconate-titanate, lead meta-niobate, lead titanate, or other ceramic crystal material. Each of the positive electrodes 96, negative electrodes 98, and piezoelectric elements 100 may have a bore extending through the center. The positive and negative electrodes 96 and 98 are electrically coupled to a wires 102 and 104, respectfully. Wires 102 and 104 transmit electrical signal from the generator 30 to electrodes 96 and 98.

As illustrated in FIG. 1, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an antinode. (For purposes of this disclosure, the term "near" is defined as "exactly at" or "in close proximity to".) It is also contemplated that the mounting device 84 may be attached to the second resonator 94 by any suitable means, and that the second resonator 94 and mounting device 84 may be formed as a single or unitary component.

The mounting device 84 is coupled to the housing 52 of the handpiece assembly 50 near a node. The mounting device 84 may also include an integral ring 108 disposed around its periphery. The integral ring 108 is preferably disposed in an annular groove 110 formed in the housing 52 of the handpiece assembly 50 to couple the mounting device 84 to the housing 52. A compliant member or material 112, such as a pair of silicone O-rings attached by stand-offs, may be placed between the annular groove 110 of the housing 52, and the integral ring 108 of the mounting device 84 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 is preferably configured to amplify the ultrasonic vibration amplitude that is transmitted through the acoustic assembly 80 to the distal end of the end effector 88. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as, for example, a stepped horn, a conical horn, an exponential horn, a unitary gain horn or the like.

The distal end of the mounting device 84 may be coupled to the proximal end of the transmission rod 86 by an internal threaded connection. It is contemplated that the transmission rod 86 be attached to the mounting device 84 by any suitable means. The mounting device 84 is preferably coupled to the transmission rod 86 near an antinode.

The transmission rod 86 may, for example, have a length substantially equal to an integral number of one-half system wavelengths ($n\lambda/2$). The transmission rod 86 is preferably fabricated from a solid core shaft constructed out of material which propagates ultrasonic energy efficiently, such as titanium alloy (i.e., Ti-6Al-4V) or an aluminum alloy. It is contemplated that the transmission rod 86 may be fabricated from any other suitable material. The transmission rod 86 may also amplify the mechanical vibrations transmitted through the transmission rod 86 to the end effector 88 as is well known in the art.

As illustrated in FIG. 1, the transmission rod 86 includes stabilizing silicone rings or compliant supports 116 positioned at a plurality of nodes. The silicone rings 116 dampen undesirable vibration and isolate the ultrasonic energy from a tubular member of a removable sheath 120 assuring the flow of ultrasonic energy in a longitudinal direction to the distal end of the end effector 88 with maximum efficiency.

As shown in FIG. 1, the removable sheath 120 is coupled to the distal end 56 of the handpiece assembly 50. The sheath 120 generally includes an adapter or nose cone 122 and an elongated tubular member 124. The tubular member 124 is attached to the adapter 122 and has an opening extending longitudinally therethrough. The sheath 120 may be threaded or snapped onto the distal end of the housing 52. The transmission rod 86 of the acoustic assembly 80 extends through the opening of the tubular member 124 and the silicone rings 116 isolate the transmission rod 86 from the tubular member 124. The adapter 122 of the sheath 120 is preferably constructed from Ultem®, and the tubular member 124 is fabricated from stainless steel. Alternatively, the transmission rod 86 may have polymeric material that surrounds the transmission rod 86 to isolate it from outside contact.

The distal end of the transmission rod 86 may be coupled to the proximal end of the end effector 88 by an internal threaded connection, preferably near an antinode. It is contemplated that the end effector 88 may be attached to the transmission rod 86 by any suitable means, such as a welded joint or the like. Although the end effector 88 may be detachable from the transmission rod 86, it is also contemplated that the end effector 88 and transmission rod 86 may be formed as a single unit.

The end effector 88 may have a distal region 88b having a smaller cross-section area than a proximal region 88a thereof, thereby forming a vibrational amplitude step-up junction. The step-up junction acts as velocity transformer as known in the art, increasing the magnitude of the ultrasonic vibration transmitted from the proximal region 88a to the distal region 88b of the end effector 88.

The end effector 88 preferably has a length substantially equal to an integral multiple of one-half system wavelengths (nλ/2). The end effector 88 is disposed at an antinode in order to produce the maximum longitudinal deflection of the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 is preferably made from a solid core shaft constructed of material which propagates ultrasonic energy, such as a titanium alloy (i.e., Ti-6Al-4V) or an aluminum alloy. It is contemplated that the end effector 88 may be fabricated from any other suitable material. It is also contemplated that the end effector 88 may have a surface treatment to improve the delivery of energy and desired tissue effect. For example, the end effector 88 may be micro-finished, coated, plated, etched, grit-blasted, roughened or scored to enhance coagulation in tissue or to reduce adherence of tissue and blood to the end effector. Additionally, the end effector 88 may be sharpened or shaped to enhance its energy transmission characteristics. For example, the end effector 88 may be blade shaped, hook shaped, or ball shaped.

Figure 2:
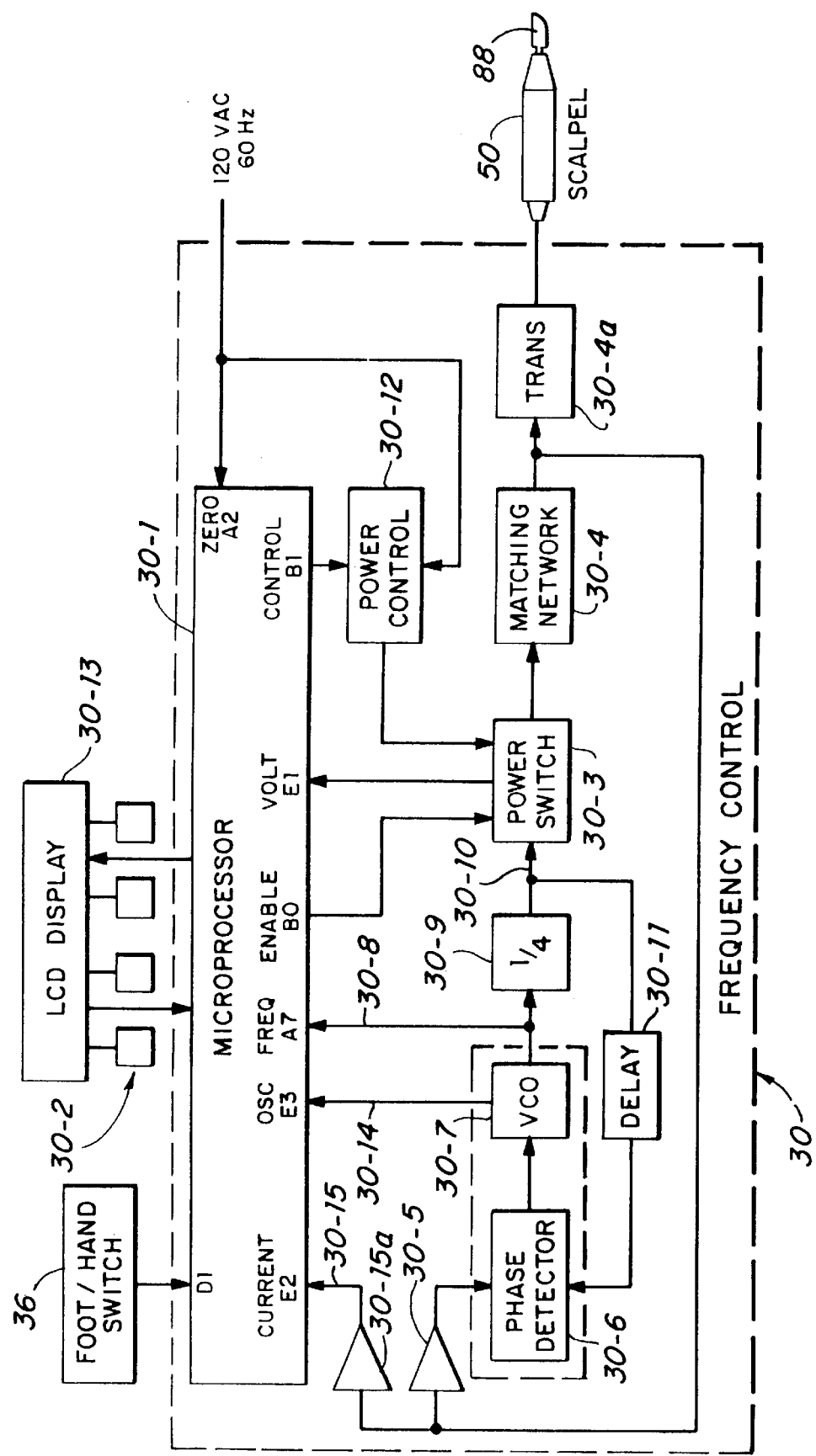
FIG. 2 is ia block diagram of a generator usable with the system of FIG. 1.

The block diagram of FIG. 2 illustrates an exemplary generator 30 of the surgical system 10. The generator 30 includes a processor 30-1, such as, for example, a programmed microprocessor which may, for example, be a Motorola model number 68HC11. The processor 30-1 is programmed to monitor appropriate power parameters and vibratory frequency as well as providing an appropriate power level in various operating modes.

The generator of the type illustrated in the block diagram of FIG. 2 is disclosed and described in U.S. Pat. No. 5,026,387 ("the '387 patent") entitled "Method and Apparatus for Ultrasonic Surgical Cutting and Hemostasis". The '387 patent is assigned to the Assignee of the present application and is incorporated herein by reference.

Manually operable controls 30-2 are provided for the purpose of enabling an operator to adjust the power level to be applied to the transducer assembly when operating. Hence, simultaneous cutting and small vessel coagulation of a predetermined level can be obtained whenever the end effector 88 is in contact with tissue.

The generator 30 includes a power output switch 30-3 which is in turn coupled to a matching network 30-4. In operation, the power switch 30-3 supplies electrical energy to the handpiece assembly 50 by way of a matching network 30-4 and an isolation transformer 30-4a. Feedback from the handpiece assembly 50, and the transducer assembly therein, is coupled via amplifier 30-5 to a phase detector 30-6.

Output from the phase detector 30-6 is fed to an input port of a voltage controlled oscillator 30-7. The voltage controlled oscillator 30-7 generates a variable frequency output signal on the line 30-8.

The signal on the line 30-8 can be divided in a divide by a four counter or network 30-9. The divided variable frequency signal is then provided on a line 30-10 as an input to the power switch 30-3, previously discussed. A delay element 30-11 provides a delay signal to the phase detector 30-6. A power control unit 30-12 is coupled between the processor 30-1 and the power switch 30-3.

An output liquid crystal display 30-13 may also be coupled to the processor 30-1. The display 30-13 is intended to provide a status information for the user or operator.

Line 30-15, which is coupled to input E2 of the processor 30-1, enables the processor 30-1 to monitor ultrasonic drive current detected at the output of the network 30-4. This line includes a root means square (RMS) to DC converter 30-15a.

An oscillator output voltage is sensed at input E3 of the processor 30-1 while an output frequency is sensed at A7 of the processor 301. Output voltage is sensed at E1 of the processor 30-1. Output BO of the processor 30-1 provides an enable signal to the power switch 30-3.

Frequency control for generating output signals from the generator 30, corresponding to a resonant frequency of the acoustic assembly 80 (carried by the handpiece assembly 50), is produced through the use of a phase lock loop which includes a phase detector 30-6 and oscillator 30-7. The phase detector 30-6 compares the phase of the output driving current and voltage signals with an error signal obtained from the phase detector used to control the voltage controlled oscillator 30-7 to thereby produce the desired output frequency. An output on a line 30-14 (input E3) from the voltage controlled oscillator 30-7 is a voltage which is proportional to the generator frequency. It is used for the purpose of monitoring to determine whether or not the frequency is within a proper operating range. The actual variable frequency output signal from the oscillator 30-7 is coupled on a line 30-8 to the processor 30-1 (input A7).

Figure 3:
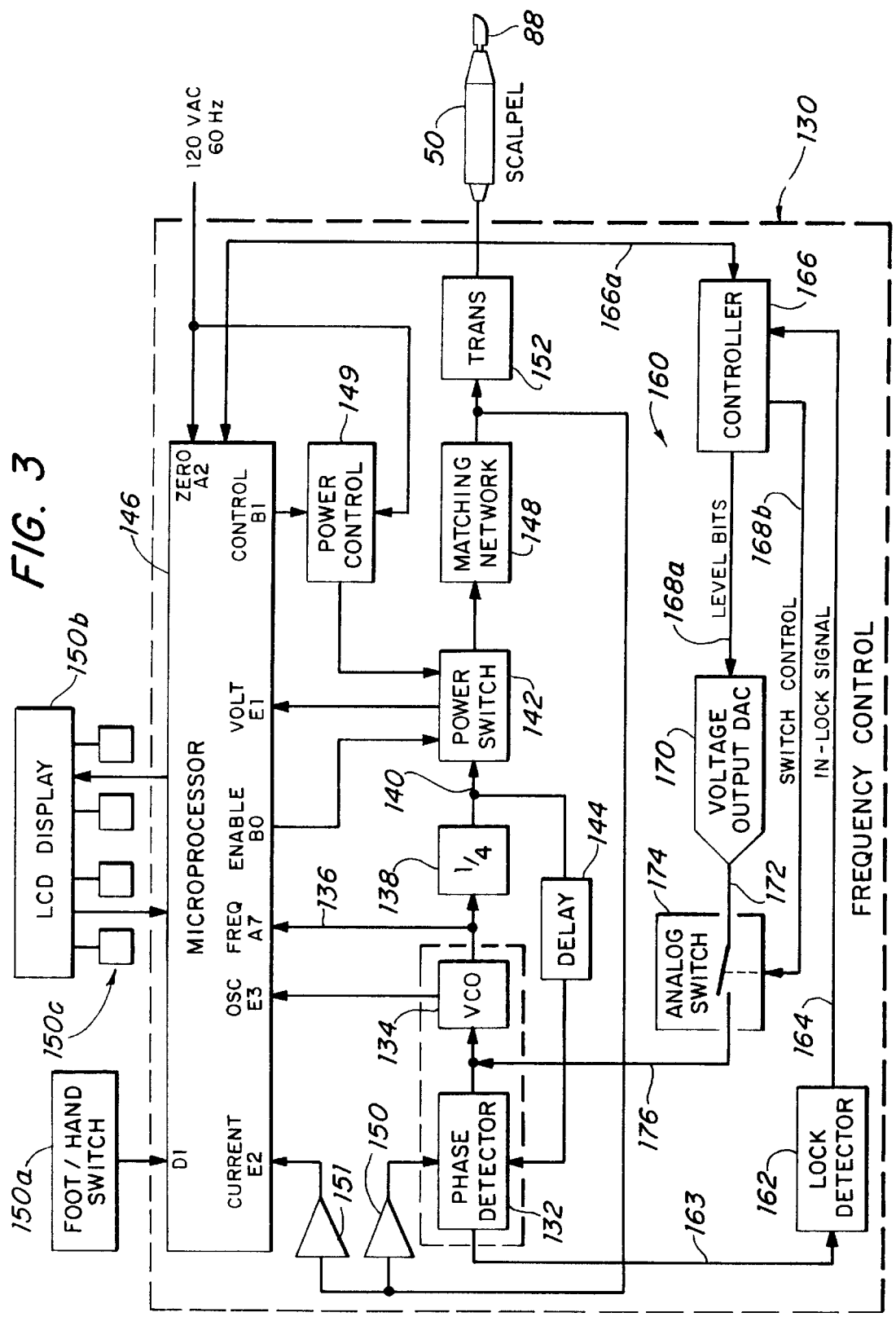
FIG. 3 is a block diagram of a generator which incorporates supervisory control circuitry.

FIG. 3 illustrates a block diagram of a generator 130 in accordance with the present invention for use with the ultrasonic system 10. The generator 130 includes phase detection circuitry 132 which is coupled to a voltage controlled oscillator 134. Elements 132 and 134 can be implemented in a single integrated circuit, such as, for example, a CD4046 circuit which incorporates a phase-lock frequency control loop.

An output of the oscillator 134 on a line 136 can in turn be coupled to a frequency divider 138. The divider 138 may include a plurality of flip-flop circuits configured as a counter to produce the frequency divider function.

The divided output signal on a line 140 is provided to a power switch 142 and to a delay feedback element 144. Further inputs to the power switch 142 are provided by a processor or supervisory control unit 146 and power control unit 149. The control unit 146 provides overall control for the generator 130. Output signals from the power switch 142 are coupled by a matching network 148 to an isolation transformer 152.

The matching network 148 converts an output square wave of the power switch 142 into a sine wave for driving the handpiece assembly 50. The output of the matching network 148, provides feedback signals via the RMS to DC converter 151 to the control unit 146, and via comparator 150 to the phase detection circuitry 132.

In a normal operational mode, the phase detection circuitry 132 and voltage controlled oscillator 134 function with established minimum and maximum operating frequencies. Output signals from the oscillator 134 in combination with feedback signals from the output of the matching network 148 establish a resonant condition at the output acoustic assembly of the handpiece assembly 50.

Under certain circumstances, control provided by the phase detection circuitry 132 and voltage controlled oscillator 134 may not be sufficient to respond to a changing environment. For example, voltage and frequency changes occur with both heating and variations in the characteristics of ultrasonic components. As a result, minimum and maximum frequencies may vary.

Physically longer ultrasonic systems, which may include larger numbers of half wave length sections, are susceptible to the presence of transverse modes of vibration and also exhibit non-fundamental modes of vibration. Hence, it is desirable to impose additional controls on minimum and maximum permissible frequency values.

Figure 3A:
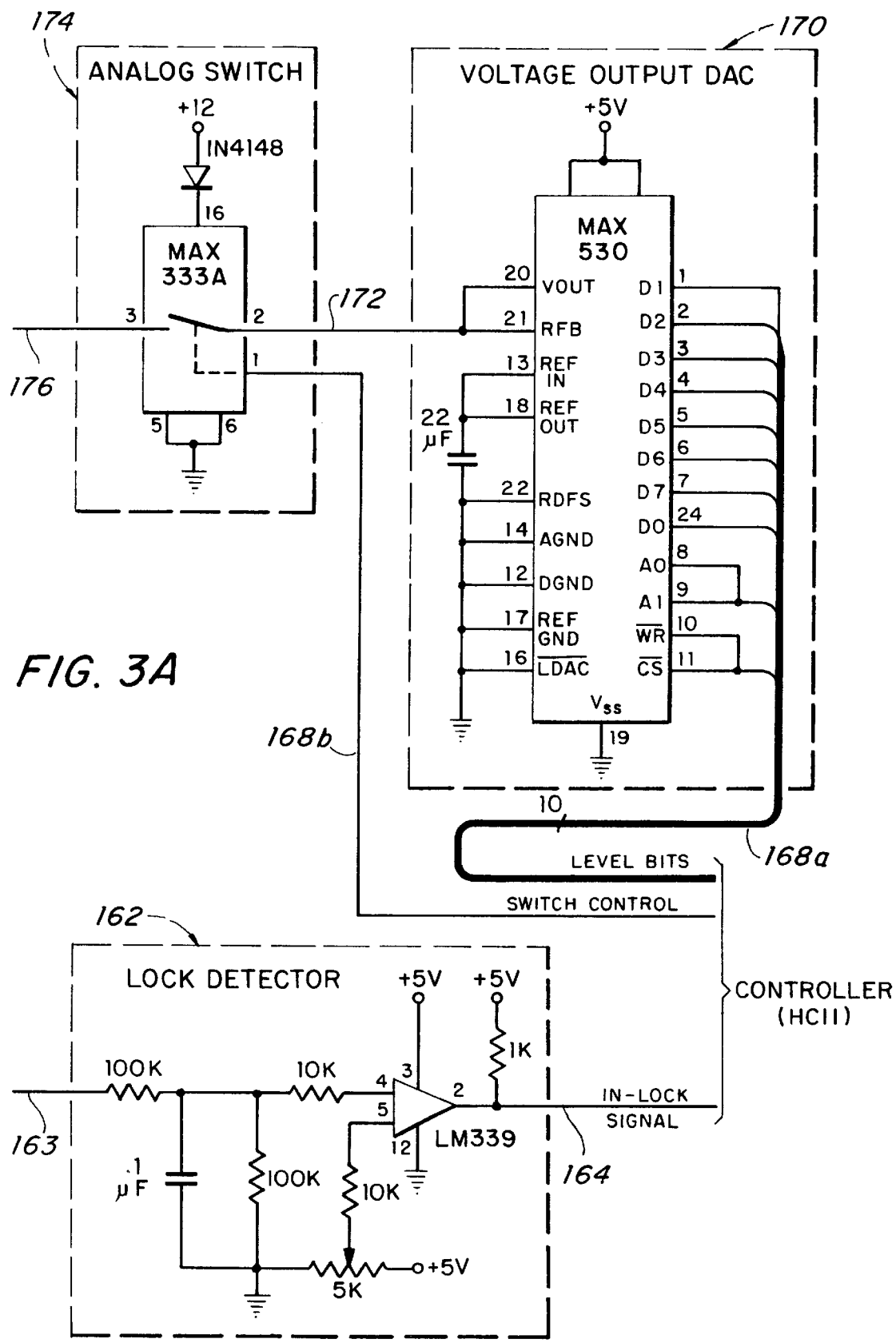
FIG. 3A is a schematic diagram of various components of the generator of FIG. 3.

In order to control transverse nodes of vibration and non-fundamental nodes of vibration of the acoustic assembly, the generator 130 includes a control feedback loop 160. The control circuitry 160 includes detector circuitry 162 which is coupled to the phase detection circuitry 132. The detector circuitry 162 senses the presence or absence of a phase locked condition in the phase detection circuitry 132 and voltage controlled oscillator 134. An exemplary circuit diagram of the detector circuitry 162 is illustrated in FIG. 3A.

The detector circuitry 162, on a line 164 provides an indication of the presence or absence of phase lock to a feedback processor unit 166, such as, for example, a programmable digital processor. It will be understood that a variety of programmable processors could be used to process the signals on the line 164 without departing from the spirit and scope of the present invention. The processor unit 166 could also be incorporated into the processor 146 (indicated by a line 166a). Alternately, the processor unit 166 could be implemented as a hard wired logic system.

The processor unit 166 has two output ports 168a and 168b. The output port 168a may include a plurality of parallel digital data lines (for example 8 or 16 bits) that provide digital input drive signals to a digital to analog converter 170. The converter 170 sends a voltage signal on a line 172 to an input of an analog switch 174. The analog switch 174 could be implemented as 333A (MAXIM), for example. An exemplary circuit diagram of the converter 170 and analog switch 174 is illustrated in FIG. 3A.

The second output port 168b of the processor unit 166 provides a control signal to a control input of the switch 174 for the purpose of causing the switch 174 to exhibit a conducting or a non-conducting state. An output of the switch 174, on a line 176, provides an override voltage control signal to the input port of the voltage controlled oscillator 134. The override voltage control signal on the line 176 overrides the signal from the phase detector 132 and provides an input to the voltage controlled oscillator 134 corresponding to a known desired condition.

In one instance, where the detector circuitry 162 indicates a loss of phase lock by the generator 130, the override control signal on the line 176 can be used to establish the last known resonant frequency exhibited by the system 10. Further, the processor unit 166 can sweep the value of the override signal on the line 176, starting from the last known resonant frequency, between minimum and maximum permissible frequency values for the system so as to quickly re-establish a resonant condition.

Once resonance has been re-established, analog switch 174 assumes an open or non-conducting state, in response to the control signal from the output port 168b. This isolation in turn enables the phase lock loop system, (i.e., elements 132, 134) to resume normal operational control of the acoustic system.

By incorporating processor unit 166 into the generator 130, tighter control can be maintained over the minimum and maximum permissible frequency values. The processor unit 166 effectively establishes frequencies in the frequency domain which in turn minimizes voltage variation effects.

A communications link 166a can be provided between the processor unit 166 and the supervisory control unit 146. Such a link in turn makes it possible for an operator, via the display 150b and inputs 150c to establish minimum and maximum frequencies, hence bandwidth, for the purpose of driving acoustic systems with significantly different fundamental frequencies. This in turn makes it possible to adjust the minimum frequency so as to drive acoustic systems having greater thermal frequency variations.

The processor unit 166 makes it possible to drive the acoustic assembly of the surgical system 10 at a predetermined fixed frequency so as to measure a non-resonant transducer assembly property. These properties would include, for example, impedance characteristics of end effectors 88.

The generator 130 is also capable of providing immediate reductions in longitudinal motion of the acoustical assembly of the surgical system 10 where desired, by altering the voltage input on the line 176 to the voltage controlled oscillator 134. The voltage on the line 176 can be altered so as to purposely drive the acoustic assembly into a non-resonant condition thereby producing an immediate reduction in motion of the end effector 88.

Additional advantages provided by the generator 130 include reduction of the time necessary to establish a resonant condition due to being able to impose greater control over a minimum and maximum frequency variations. Recovery time to a resonant condition is reduced by being able to retrieve the frequency associated with a recent successful resonant condition from storage. The stored value, representative of resonant frequency, can in turn be used as a starting point for purposes of varying drive frequency to the system while searching for an acceptable resonant condition.

Output voltage from the digital to analog converter 170 can also be used for the purpose of identifying acoustic systems with unique resonance profiles. This can be carried out by driving the converter 170 as a programmable frequency generator. Finally, the same operational characteristics can be used for evaluating the performance of acoustical systems.

Figure 4A:
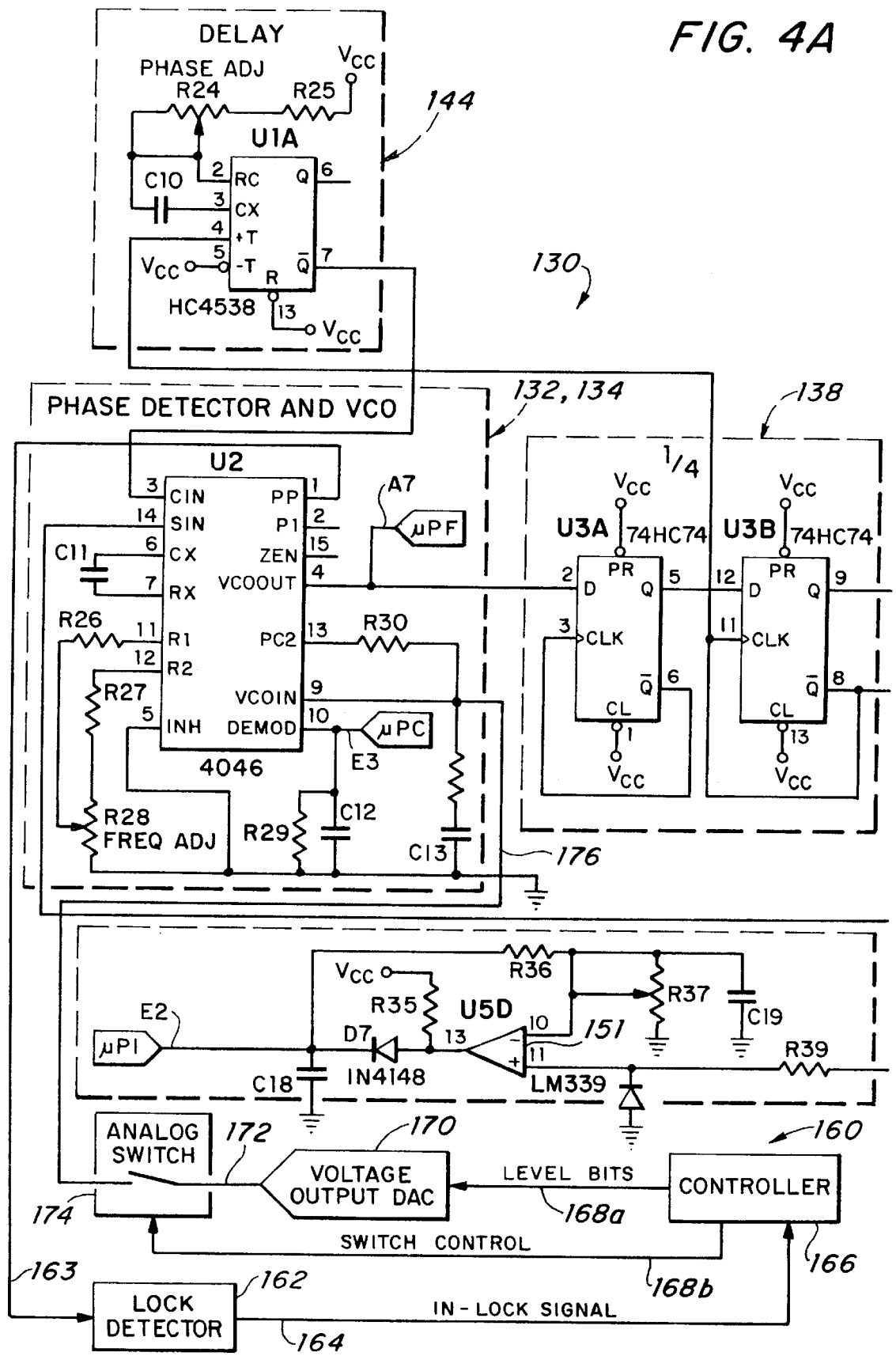
FIGS. 4A and 4B are a schematic diagram of various components of the generator of FIG. 3.

FIGS. 4A and B are a schematic diagram of various components of the generator 130. As illustrated in FIG. 4A, the phase lock loop system, elements 132, 134 can be implemented by means of a 4046 integrated circuit. Frequency divider circuitry 138 can be implemented as two series coupled D-type flip-flop circuits.

Figure 4B:
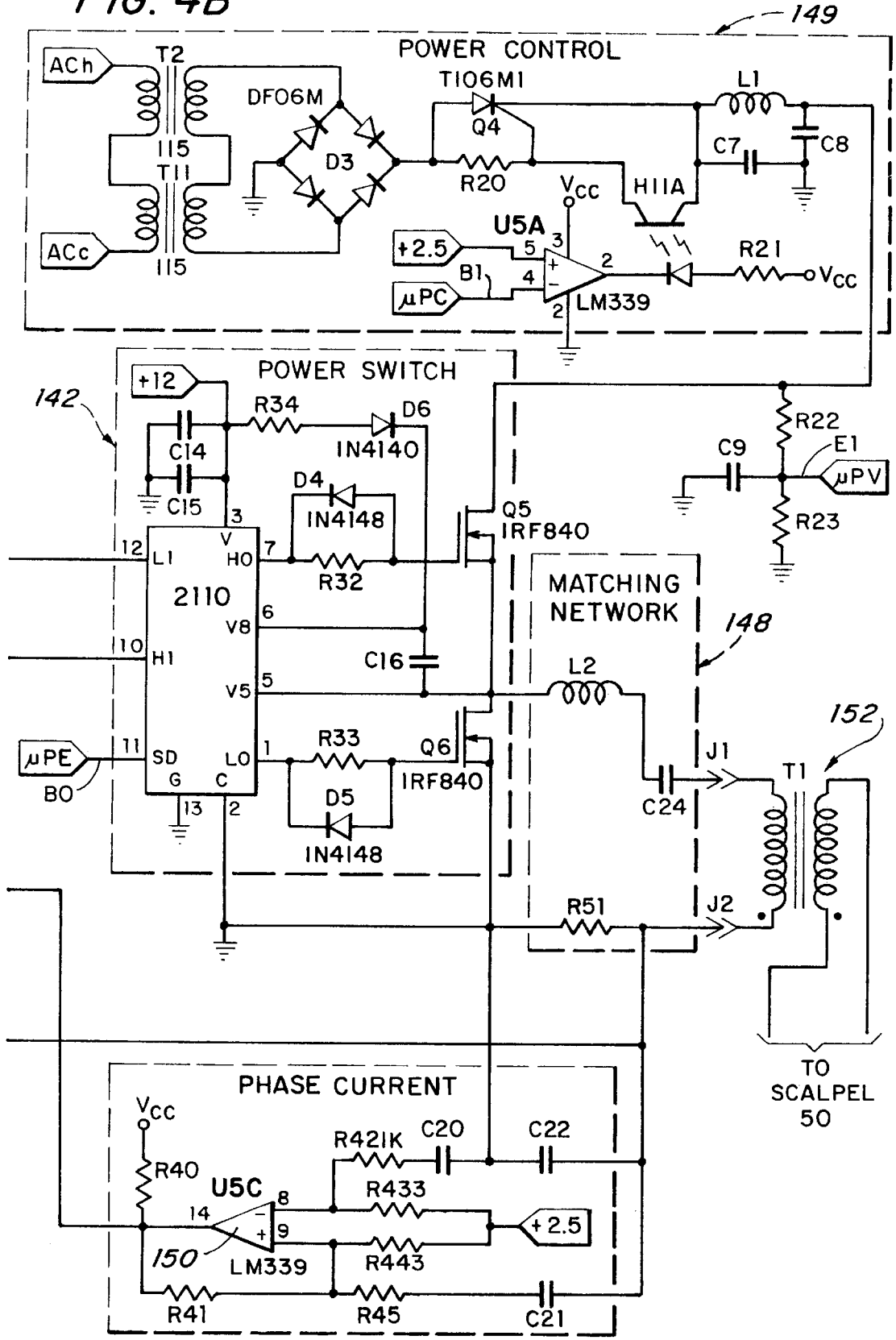

Power switch control 142 (see FIG. 4B) incorporates an IR2110 field effect switches Q5, Q6 which in turn are coupled to the matching network 148. The network 148 incorporates an LC filter for converting pulses from the power switch to a sine wave-like output signal. The delay 144, as illustrated in FIG. 4A, can be implemented by means of a monostable multivibrator. Feedback is also provided via comparator 150, illustrated in FIG. 4B as an LM339 integrated circuit.

Input to the lock detection circuitry 162 can be obtained from a phase pulse output line, such as pin 1 of the 4046 integrated circuit on line 163. Output voltages from the control loop 160, on the line 176 can be coupled to the voltage input port, pin 9 of the 4046 integrated circuit.

Microprocessor 146 could be implemented using a Motorola type 68HC11 programmable microprocessor. Other types of microprocessors can be incorporated without departing from the spirit and scope of the present invention.

Figure 5:
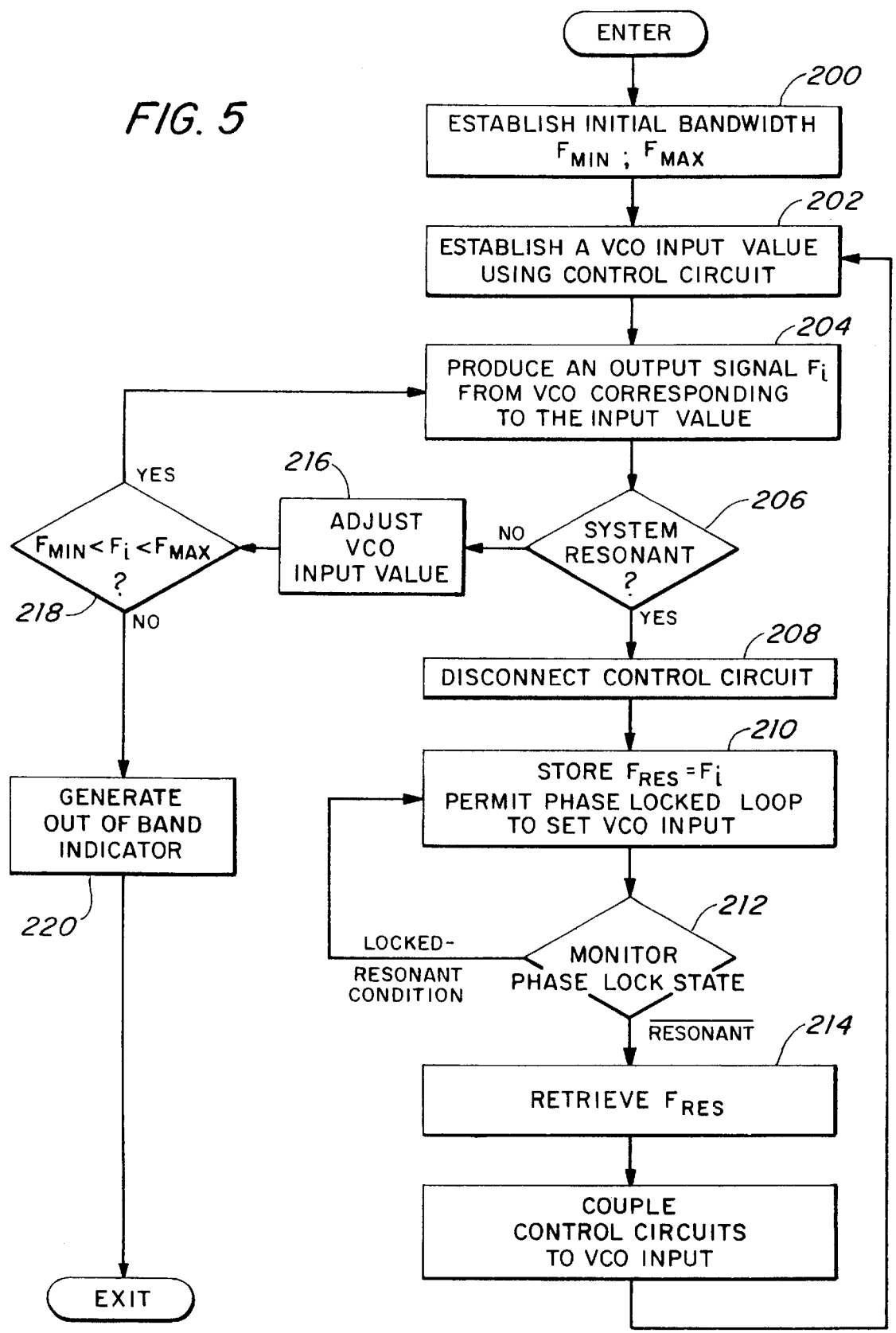
FIG. 5 is a flow diagram of a control method implementable by the generator of FIG. 3.

FIG. 5 illustrates a flow diagram of a method of controlling the acoustic assembly of the surgical system so as to detect abnormal operational conditions and return to a resonant condition. In an initial step 200, a transducer frequency range specified by $F_{min}$ and $F_{max}$ is established and stored. In a step 202 supervisory circuitry 160 can be used to establish an initial input voltage value for the voltage controlled oscillator 134. In a step 204, the oscillator 134 produces the desired frequency which is in turn coupled to the acoustic assembly of the surgical system.

In a step 206, the control circuitry 160 determines whether or not the acoustic assembly 50 is being operated in a resonant condition. If so, in a step 208 the control circuitry 160 is decoupled. In a step 210, a representation of the current resonant frequency FRES is stored and the phase lock loop system 132, 134 commences control of the output to the acoustic assembly.

In a step 212, the circuitry 160 continues to monitor the presence or absence of a resonant condition. If the phase lock loop system 132, 134 has failed to maintain a resonant condition in a step 214, the most recently stored representation of a resonant frequency FRES can be retrieved from a storage element by the processor unit 166 and then used in step 202 to establish a new input to the voltage controlled oscillator 134 for the purpose of re-establishing resonance. That input can then be swept between the minimum and maximum permissible frequency values if need be to find a new resonant condition.

In the event that resonance is not initially achieved in step 206, the input voltage value to the voltage controlled oscillator 134 can be adjusted in a step 216. In a step 218 the adjusted value can be checked to determine that it is still within the acceptable range between minimum and maximum preset frequency values. If so, it can then can be used to generate a new output frequency in the step 204. In the event that resonance cannot be achieved within the preset bandwidth, an error condition can be indicated at a step 220.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. An ultrasonic surgical device comprising:
   a transducer assembly adapted to vibrate at an ultrasonic frequency in response to electrical energy,
   circuitry generating an output signal having a desired frequency to drive the transducer assembly at a resonant condition, the circuitry providing a resonant condition restoring signal to the transducer assembly in response to detecting a non-resonant condition of the transducer assembly, the resonant condition restoring signal including a most recently stored resonant frequency;
   a transmission rod having a first end and a second end, the transmission rod being adapted to receive the ultrasonic vibration from the transducer assembly and to transmit the ultrasonic vibrations from the first end to the second end of the transmission rod; and
   an end effector having a first end and a second end, the end effector being adapted to receive the ultrasonic vibrations from the transmission rod and to transmit the vibrations from the first end to the second end of the end effector, the first end of the end effector being coupled to the second end of the transmission rod.

2. An ultrasonic system comprising:
   a variable frequency, closed loop, oscillator with an input port and an output port wherein an output signal is generated at the output port in response to an applied electrical signal at the input port;
   an ultrasonic transducer having a selected resonant frequency wherein the transducer is coupled to the output port;
   a feedback circuit coupled between the transducer and the input port for applying an electrical signal to the input port with a value corresponding to the selected resonant frequency whereby the transducer will be driven in a resonant condition; and
   a control circuit coupled to the input port wherein the control circuit includes sensing circuitry for detecting a non-resonant condition and wherein in response thereto the control circuit provides a resonant condition restoring signal to the input port, the resonant condition restoring signal including a most recently stored resonant frequency.

3. The system as in claim 2 wherein the control circuit includes a controller unit with an input port coupled to the sensing circuitry.

4. The system as in claim 3 wherein the controller unit includes a programmable digital processor.

5. The system as in claim 3 wherein the controller unit includes first and second output ports wherein one of the controller output ports is coupled to a digital-to-analog converter with an analog output coupled to the input port.

6. The system as in claim 5 wherein the control circuit includes a solid state isolation switch coupled between the analog output and the input port with a switch control line coupled to the other output port of the controller unit.

7. The system as in claim 2 wherein the control circuit includes a digital-to-analog converter coupled between the input port and a phase output of the oscillator.

8. The system as in claim 7 wherein the control circuit includes a storage element wherein a representation of a resonant frequency is stored.

9. The system as in claim 7 wherein the control circuit includes a storage element for storing maximum and minimum operational frequency values.

10. The system as in claim 7 wherein the control circuit includes a storage element for storing a preselected bandwidth parameter.

11. A variable frequency generator for providing electrical signals in a predetermined range to a transducer assembly, the generator comprising:
    an oscillator which includes an output port and a phase locked feedback loop for providing feedback signals for maintaining the frequency of an output signal at the output port within the predetermined range;
    a second feedback loop coupled to the oscillator and to the phase locked feedback loop wherein in response to a predetermined condition, the second feedback loop generates an override feedback signal which establishes at least one preset frequency for the output signal.

12. The generator as in claim 11 wherein the phase locked feedback loop includes a resistor and a capacitor coupled together at a node and wherein the override feedback signal is coupled thereto.

13. The generator as in claim 11 wherein the second feedback loop includes a control circuit for generating frequency determining feedback signals in response to a detected electrical parameter of the oscillator system indicating a non-resonant condition, wherein the control circuit includes an enable output and a magnitude output indicative of a desired output frequency and wherein the magnitude output is coupled to the phase locked feedback loop in response to the presence of the enable signal.

14. The generator as in claim 13 further including a digital-to-analog converter coupled between the magnitude output and the phase locked feedback loop.

15. The generator as in claim 14 further including a solid state switch with a signal input, a signal output and a control input wherein the signal input is coupled to the digital-to-analog converter, the signal output is coupled to the phase locked feedback loop and the control input of the switch is coupled to the enable output of the control circuit.

16. The generator as in claim 13 wherein the control circuit includes a programmable digital processor and circuitry for varying an amplitude value, over a preset range, on the magnitude output.

17. The generator as in claim 16 wherein the control circuit includes a sensor coupled between the phase locked feedback loop and the digital processor.

18. The generator as in claim 13 wherein the control circuit includes a storage device for storing a representation of a frequency at which the transducer exhibited resonance.

19. The generator as in claim 13 wherein the control circuit includes circuits for storing a predetermined bandwidth parameter.

20. A generator for use with an ultrasonic instrument comprising:
    an adjustable source of electrical signals wherein the source includes a first input port and a variable frequency output port for providing variable frequency output signals within a predetermined range;
    a switch element, coupled to the output port, and adapted to provide variable frequency drive signals to the instrument;
    a first feedback loop, coupled to the first input port and adapted to receive at least one electrical feedback signal from the instrument wherein feedback signals from the loop vary signals at the variable frequency output within the predetermined range; and
    a second feedback loop coupled to the source for providing supplemental phase related feedback signals to the input port in response to the presence of a non-resonant condition wherein the phase related signals are converted from a digital to an analog form in a digital-to-analog converter and are adapted to restore a resonant condition.

21. A method of driving an ultrasonic transducer assembly comprising the steps of:
    providing a drive signal to the transducer at a resonant frequency thereby establishing a resonant condition;
    adjusting the frequency in response to feedback signals to maintain the resonant condition;
    monitoring a selected parameter indicative of the resonant condition and in response to a loss of the resonant condition, generating a separate frequency establishing control signal having a most recently stored resonant frequency, and adjusting the frequency of the drive signal in response thereto; and
    monitoring the selected parameter and in response to re-establishing a resonant condition, removing the frequency establishing control signal.

22. The method as in claim 21 further including the step of storing bandwidth establishing information.

23. The method as in claim 22 further including the step of sweeping the value of the control signal so as to sweep the frequency of the drive signals across the prestored bandwidth in attempting to re-establish a resonant condition.

24. The method as in claim 22 further including the step of storing a representation of a resonant frequency and in response to the loss of the resonant condition, generating a control signal having a value corresponding to the stored representation.

25. The method as in claim 22 further including the step of isolating the separate frequency control signal before the generating step.

26. The method as in claim 23 wherein the feedback signals include a phase indicative component and including isolating the frequency establishing control signal from at least the phase indicative component before the generating step.

27. The method as in claim 26 further including the step of coupling the frequency establishing control signal to the phase indicative component until a resonant condition has been established.

28. The method as in claim 26 further comprising the step of altering the drive signal to reduce longitudinal motion of an acoustical assembly.

29. The method as in claim 26 further comprising the step of measuring non-resonant properties of the transducer assembly.

30. A generator for providing electric signals to a transducer assembly comprising:
- a phase lock loop generating an output signal having a desired frequency;
- detector circuitry to detect a non-resonant condition of the phase lock loop; and
- a processing unit coupled to the detector circuitry to provide an input signal to the phase lock loop of a desired condition.

31. The generator of claim 30 further including a digital to analog circuit coupled to the processing unit.

32. The generator of claim 31 further including a switch coupled to the analog circuit, the phase lock loop, and the processing unit.

33. The generator of claim 32 wherein the detector circuitry re-establishes a resonant condition.

* * * * *